United States Patent [19]
Löhn et al.

[11] Patent Number: 6,065,966
[45] Date of Patent: May 23, 2000

[54] MEDICAL OR DENTAL TREATMENT INSTRUMENT FOR THE TREATMENT OF BODY TISSUE OR A SUBSTITUTE MATERIAL, IN PARTICULAR BY CUTTING, AND TOOL FOR SUCH A TREATMENT INSTRUMENT

[75] Inventors: Gerd Löhn, Biberach/Rissegg; Gerhard Krause, Warthausen; Walter Mössle, Mittelbiberach, all of Germany

[73] Assignee: Kaltenbach & Voigt GmbH & Co., Biberach, Germany

[21] Appl. No.: 09/193,529

[22] Filed: Nov. 17, 1998

[30] Foreign Application Priority Data

Nov. 21, 1997 [DE] Germany .......................... 197 51 682

[51] Int. Cl.⁷ ....................................................... A61C 1/14
[52] U.S. Cl. ............................................................. 433/128
[58] Field of Search .................................... 433/127, 128, 433/165; 606/80

[56] References Cited

U.S. PATENT DOCUMENTS

| | | | |
|---|---|---|---|
| 462,896 | 11/1891 | Eddy | 433/128 |
| 1,267,629 | 5/1918 | Chayes | 433/128 |
| 2,010,210 | 8/1935 | Witt | 433/128 |
| 4,234,308 | 11/1980 | Leonard | 433/127 |
| 4,940,410 | 7/1990 | Apap et al. | 433/128 |
| 5,028,181 | 7/1991 | Jenkins et al. | 433/128 |
| 5,078,605 | 1/1992 | Sutter et al. | 433/165 |
| 5,584,689 | 12/1996 | Loge | 433/128 |

FOREIGN PATENT DOCUMENTS

| | | |
|---|---|---|
| 4408574 A1 | 7/1993 | Germany . |
| WO 96/14024 | 5/1996 | WIPO . |

*Primary Examiner*—John J. Wilson
*Attorney, Agent, or Firm*—Marshall, O'Toole, Gerstein, Murray & Borun

[57] ABSTRACT

In the case of a medical or dental treatment instrument for the treatment of body tissue or a substitute material, in particular by cutting, with an elongated handpiece which in its front end region comprises a retaining device with a plug-in hole, into which the tool with its tool shank is capable of being inserted and is capable of being locked by means of a locking part which is movably supported transversely in relation to the tool shank between a locking position in which it is set into a locking recess in the tool shank and a release position releasing the tool shank and is pressurised into its locking position by the force of a spring, an actuating member which is manually accessible from outside is provided which is movably supported on the retaining device and with which the locking part is capable of being displaced into its release position, the actuating member being displaceably supported transversely in relation to the tool shank.

17 Claims, 7 Drawing Sheets

MEDICAL OR DENTAL TREATMENT INSTRUMENT FOR THE TREATMENT OF BODY TISSUE OR A SUBSTITUTE MATERIAL, IN PARTICULAR BY CUTTING, AND TOOL FOR SUCH A TREATMENT INSTRUMENT

BACKGROUND OF THE INVENTION

In medical or dental technology a treatment of the human body or the body of an animal or artificial parts thereof (prostheses) with a treatment instrument can be effected in various ways. In many cases only a treatment of the body is required, without changing its shape. It may be a question, for example, of a surface treatment which, for example, can be carried out with a treatment instrument having a special tool for the surface treatment, in which connection it may be a question, for example, of a massage treatment or an application of a therapeutic medium to the body. A different type of treatment consists, for example, in changing the shape of the body, such as is the case, for example, with processing involving removal of material by cutting, in the course of which, for example, a cut is made in the body tissue. Cutting treatments also include the preparation of a cavity with a cutting tool, or the surface treatment of a tooth in order to remove a coating, for example. Tools used for cutting may be, for example, rotary tools such as drills and milling cutters, files and those tools having at least one working surface that is abrasive in two dimensions—ie, that is studded with a plurality of cutting edges or cutting points arranged alongside one another, the tool being driven in oscillating manner by a vibrating drive. Such a treatment instrument or tool is described, for example, in WO 96/14024.

A great many demands are made of a treatment instrument of the present type. One requirement is that the treatment instrument should be of small or slim structural design, in order that the view of the treatment site is not impaired or is only negligibly impaired. Inasmuch as several different treatment tools are present in the case of a treatment instrument of the present type, the retaining device should enable an easy-to-handle and rapid exchange of the tools, so that the treatment instrument can be employed with appropriate power for different types of treatment. In the case of a treatment instrument that is known from WO 96/14024, for the purpose of retaining the tool on a protruding shank of the treatment instrument a transverse hole is provided in the shank, into which the tool shank is capable of being inserted and is capable of being locked to prevent it from slipping out by means of a fixing element which is capable of being displaced between a locking position set into a device for locking the tool shank and a release position releasing the tool shank and is biased into its locking position by the force of a spring. In the stated printed publication several embodiments of a retaining device for a tool are described. Inter alia it is possible to lock the tool so that it is capable of rotating freely about its longitudinal axis or capable of being immobilised in the retaining device in different rotary positions. In the case of a treatment instrument of the present type that can be inferred from the previously known DE 44 08 574 A1, for the purpose of locking the tool in the retaining device of the treatment instrument a plurality of spheres are arranged in distributed manner on the periphery of the retaining device which are capable of being pressed radially inwards by means of an inner conical surface of an axially displaceable actuating element into a locking position in which they are set into spherical indentations of the tool shank and, after a preceding axial displacement of the actuating part in the course of withdrawing the tool shank from the retaining device, are capable of being driven radially outwards into a release position. It has also already been proposed to configure a retaining device in such a way that in the course of axial displacement of the tool, for example in order to introduce it into the retaining device or to withdraw it therefrom, the locking parts are capable of being automatically driven into their release position releasing the tool shank.

SUMMARY OF THE INVENTION

The object underlying the invention is to configure a treatment instrument of the present type in such a way that, whilst guaranteeing a small or compact structural design, easy-to-handle actuation is possible in the course of locking or fixing and/or detaching and/or exchanging a tool.

This object is achieved by virtue of a medical or dental treatment instrument for the treatment of body tissue or a substitute material, in particular by cutting, with an elongated handpiece (1)

which in its front end region comprises a retaining device (6) with a plug-in hole (27) into which the tool (7) with its tool shank (8) is capable of being inserted and is capable of being locked by means of a locking part (29), which is movably supported transversely in relation to the tool shank (8) between a locking position in which it is set into a locking recess (28) in the tool shank (8) and a release position releasing the tool shank (8) and is pressurised into its locking position by the force of a spring, whereby an actuating member (91) which is manually accessible from outside is provided which is movably supported on the retaining device (6) and with which the locking part (29) is capable of being displaced into its release position, and whereby the actuating member (91) is supported so as to be capable of being displaced transversely in relation to the tool shank (8).

This object is also achieved by virtue of a medical or dental treatment instrument for the treatment of body tissue or a substitute material, in particular by cutting, with an elongated handpiece (1)

which in its front end region comprises a retaining device (6) with a plug-in hole (27) into which the tool (7) with its tool shank (8) is capable of being inserted and is capable of being locked by means of a locking part (29), which is movably supported transversely in relation to the tool shank (8) between a locking position in which it is set into a locking recess (28) in the tool shank (8) and a release position releasing the tool shank (8) and is pressurised into its locking position by the force of a spring (103), whereby in the event of an axial displacement of the tool shank (8) the locking part (125a) is automatically driven out of the locking recess (28) by a force exceeding a certain magnitude, whereby an actuating member (91) which is manually accessible from outside is provided, with which the tool shank (8) is capable of being displaced, and whereby the actuating member (91) is a component which is movably supported on the retaining device (6) between a retaining position and a push-out position.

With both configurations according to the invention the actuating member for detaching the retaining device is an add-on part of the retaining device which is movably integrated into the retaining device between a locking position locking the tool and a release position releasing it. As a result, by reason of its integration into the retaining device the actuating member cannot be lost and it is permanently available in an easy-to-handle position for actuation. At the same time it is possible, within the scope of the invention, for a small structural design to be realised, so that the view of the treatment site is not impaired or is only negligibly impaired, and which in addition can be operated in easy-to-handle manner, as a result of which the utility of the treatment instrument and the suitability thereof also for inaccessible treatment sites, as is the case in particular in the oral space of a patient, are enhanced.

In addition, both configurations according to the invention enable easy-to-handle locking and/or detaching of the tool and/or exchange of different tools, in which connection the actuating member can be actuated or grasped comfortably. The tool can also be easily pushed or drawn out of the plug-in hole, in which connection, when the locking part is moveably or rigidly connected to the actuating member, the locking part with the actuating member can be moved or driven out of the locking recess in the initial region of this movement. Said actuating member is particularly easy to operate when a reduction gear or a wedge-face mechanism is interposed.

The invention also relates to a tool preferably having at least one abrasive working surface that is capable of being activated by an oscillating drive, whereby the shank of the tool comprises retaining recesses which, whilst guaranteeing simple and inexpensive manufacture and also easy-to-handle insertion or extraction of the tool, guarantee advantageous axial retention and optionally also rotary-location positioning of the tool.

The subordinate claims contain features that further enhance the treatment instrument or the retaining device in the sense of a small structural design which can be produced inexpensively and operated in easy-to-handle manner and at the same time can enable secure acceptance and retention of the tool in the retaining device as well as ejection of said tool from the retaining device for the purpose of detaching or exchanging a tool.

BRIEF DESCRIPTION OF THE DRAWINGS

The invention and further advantages that can be achieved with it are elucidated more fully below on the basis of preferred configurations and drawings. Illustrated are.

DESCRIPTION OF THE PREFERRED EMBODIMENTS

Figure 1:
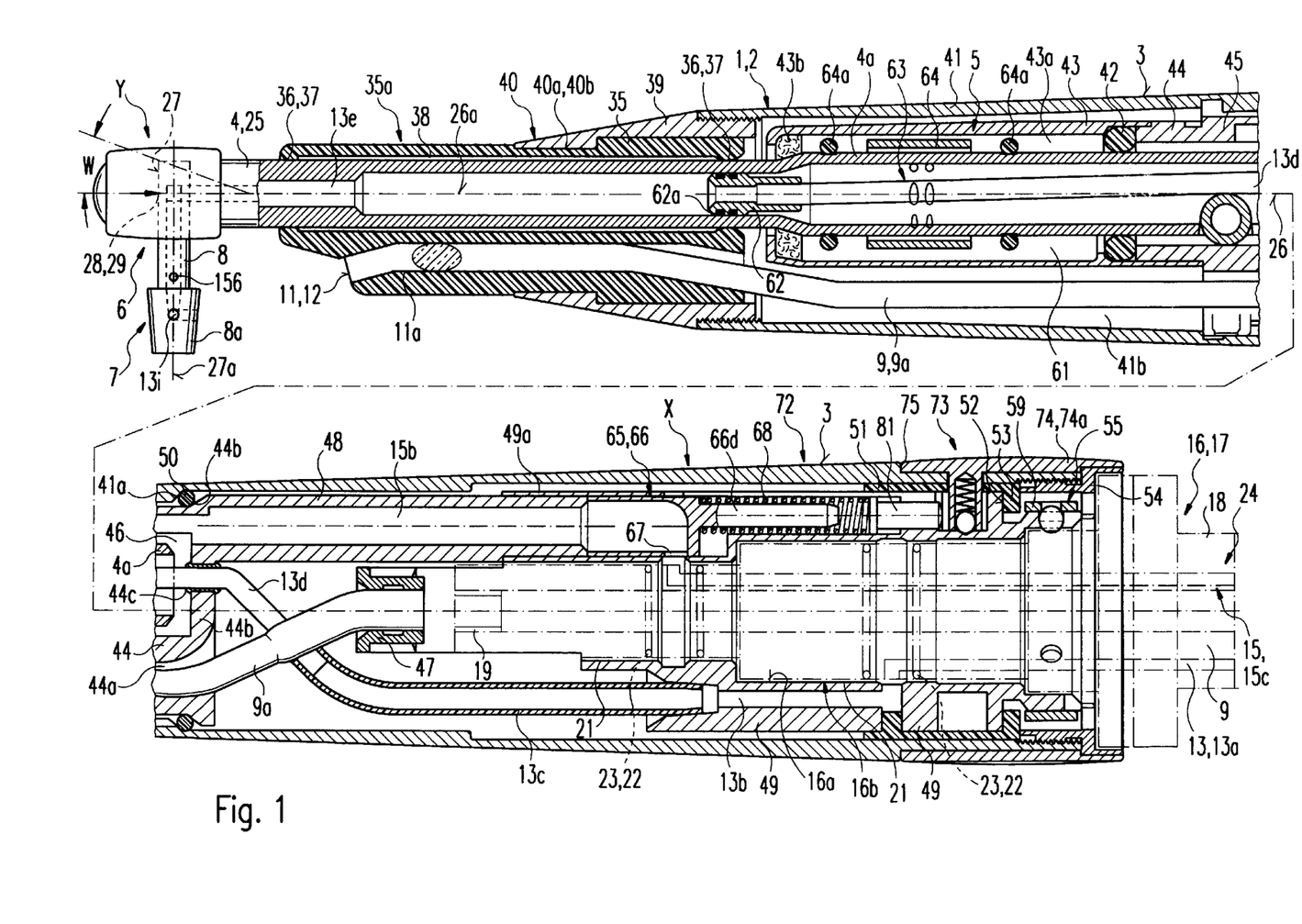
FIG. 1 a treatment instrument according to the invention for the treatment of body tissue or a substitute material, in axial section.

The main parts of the treatment instrument generally designated by 1 are an elongated or rod-shaped handpiece 2 with a gripping sleeve 3 in which a preferably elongated or rod-shaped oscillating part 4 is supported so as to be capable of oscillation and which by means of an oscillation exciter 5 is capable of being caused to oscillate or capable of being driven and a retaining device 6 for at least one treatment tool 7 which comprises a tool shank 8 which is capable of being detachably connected to the retaining device 6.

Figure 4:
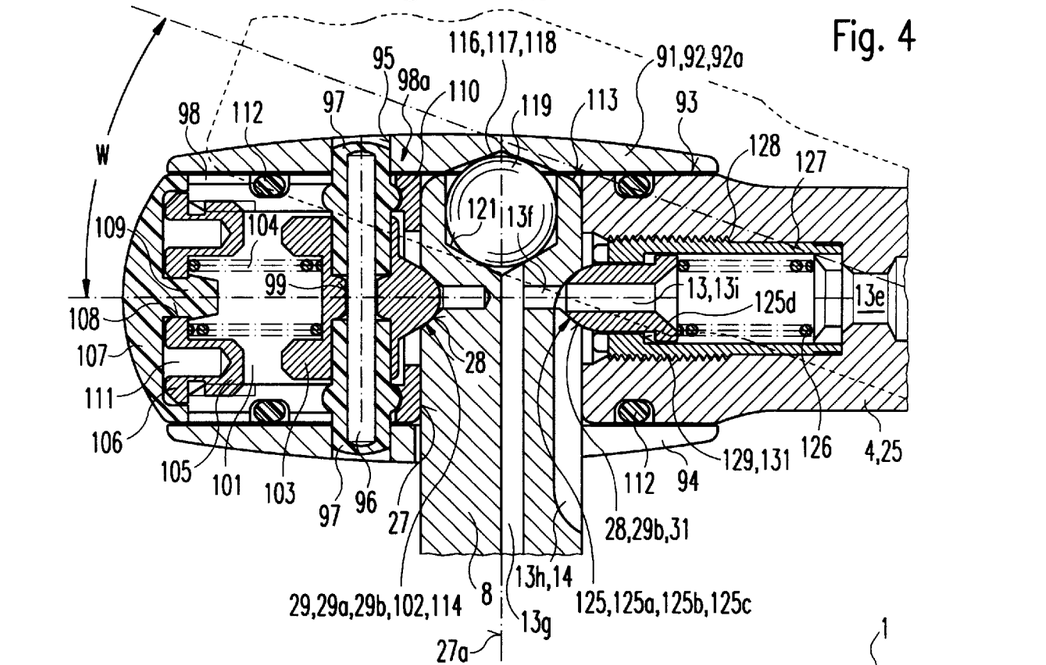
FIG. 4 the detail denoted by Y in FIG. 1, namely a retaining device for a tool arranged in the front end region of the treatment instrument, in axial section.

It is advantageous to configure the treatment instrument 1 with at least one, preferably several, so-called media lines which serve for the supply of drive energy and therapeutic media such as, for example, a therapeutic liquid and/or compressed air and for the supply of light to the treatment site. With the present configuration a lighting circuit 9 is provided which extends lengthwise through the handpiece 2 as far as the front end region thereof and opens out at an outlet opening 11 directed towards the treatment site and forms an illuminating device 12. In addition, a line 13 for a therapeutic or cooling liquid, here water, extending lengthwise through the handpiece 2 is provided which likewise opens out at an outlet opening 14 arranged in the front end region of the handpiece 2 and directed towards the treatment site (FIGS. 4 and 7) and forms a supply device.

Furthermore, a supply line 15 for drive energy is provided which extends lengthwise through the handpiece 2 as far as the drive of the oscillation exciter 5. With the present configuration an oscillation exciter 5 is provided which is capable of being driven by compressed air, and the supply line 15 is a compressed-air line which extends to the oscillation exciter 5.

The handpiece 2 is capable of being detachably connected by means of a quick coupling or by means of a screw coupling or plug-in coupling, in particular by means of a freely rotatable plug-in/rotating coupling 16, at the rear to a connecting piece 17 which is indicated and which is connected by means of a flexible supply line 18 to a supply and control device which is not represented. The plug-in/rotating coupling 16 is formed in the present configuration by a hollow cylindrical or graduated hollow cylindrical coupling recess 16*a* and a cylindrical or graduated cylindrical coupling spigot 16*b* which is capable of being inserted therein subject to clearance, whereby with the present configuration the coupling recess 16*a* is arranged in the rear region of the handpiece 2 and the coupling spigot 16*b* protrudes from the connecting piece 17. The media lines pass through the plug-in/rotating coupling 16, so that in the event of an optional separation of the handpiece 2 from the connecting piece 17 the media lines are automatically interrupted. The lighting circuit 9 passes through the plug-in/rotating coupling 16 coaxially. In this connection a rear lighting-circuit section may extend coaxially in a corresponding receiving bore as far as the front end region of the coupling spigot 16b which is adjoined, with a separation joint, by a front lighting-circuit section which extends as far as the outlet opening 14. The front lighting-circuit section is preferably formed by an optical waveguide 9a consisting of light- conducting material such as, for example, glass or plastic, whereby it may be a question of a flexible optical waveguide or a rigid optical waveguide 9a in the form of a moulding. The cross-sectional shape of the optical waveguide 9a is preferably circular at the rear and elliptical further forward. The rear lighting-circuit section may likewise be formed by an optical waveguide which is not represented or by an electrical line with a lamp 19 arranged in the front end region of the coupling spigot 16b, said lamp being arranged in a recess that is open at the front, preferably in countersunk manner.

The two other media lines 13, 15 pass through the hollow cylindrical separation joint 21 between the coupling spigot 16b and the wall of the coupling recess 16a radially from inside to outside in the shape of a Z, the openings that are present in each instance in the shell surface of the coupling spigot 16a and in the internal shell surface of the coupling recess 16b being situated in an annular groove 22 in the shell surface or in the internal shell surface. By this means the passage of media in any rotary position of the plug-in/rotating coupling 16 is also guaranteed beyond 360°. The Z-shaped penetration points are sealed in each instance by a packing ring 23, in particular by an O- ring seal, which is arranged on both sides of the Z-shaped penetration point in an annular groove in the shell surface of the coupling spigot 16b or in the internal shell surface of the coupling recess 16a. Terminals, for example ferrule terminals 24, for media-line sections located in the flexible supply line 18 may be arranged at the rear on the connecting piece 17.

The retaining device 6 for the tool 7 is arranged in the front end region of the oscillating part 4. With the present configuration the oscillating part 4 is a rod- shaped or sleeve-shaped body which is arranged in the front half of the handpiece 2 and forms a handpiece shank 25 which protrudes from the front end of the handpiece 2 and may extend in a straight line or may include an acute angle W of about 10 to 30°, in particular about 20°, with respect to the longitudinal centre axis 26 of the handpiece 2. The retaining device 6 comprises a plug-in hole 27 which extends transversely or preferably at a right angle to the handpiece shank 25 and which is preferably a blind hole and is consequently open on one side only and into which the tool shank 8 is capable of being inserted subject to slight clearance. With a view to locking the tool 7 in the inserted position, a locking recess 28 is provided in the tool shank 8, into which a locking part 29 is capable of being moved which is adjustable in the longitudinal direction of the handpiece shank 25 and adjustable between its locking position that is moved into the locking recess 28 and a moved-out release position releasing the tool shank 8 and is preferably pressurised into its locking position by the force of a spring. The locking recess 28 may be an annular groove. Several spherical indentations arranged on the periphery in evenly distributed manner may also be provided which may preferably comprise conical depressions with a central free core bore.

The handpiece shank 25 extending in the region of the handpiece 2 in the form of an oscillating rod 4a is supported in the handpiece 2 in radially and preferably also axially yielding or movable manner against elastic restoring forces. This purpose is served in the front end region of the handpiece 2 by a bearing sleeve 35 made of elastic material, for example plastic or rubber, in the through-hole 36 of which the oscillating rod 4a is received with peripheral contact so that it is centred by the bearing sleeve 35. With the present configuration the bearing sleeve 35 comprises, in its front and rear end regions, bearing beads 37 protruding radially inwards and preferably rounded in cross-section, between which an annular gap 38 is arranged surrounding the oscillating rod 4a. The bearing sleeve 35 may be firmly arranged in a sleeve cap 39 which is fly connected to a sleeve casing 41, for example screwed therein as FIG. 1 shows, and which terminate with one another in stepless manner on the periphery and form the gripping sleeve 3.

The bearing sleeve 35 protrudes beyond the sleeve casing 41 or the sleeve cap 39 and therefore forms a protective sheath 35a for the handpiece shank 25, which extends as far as, or into the vicinity of, the retaining device 6 or an actuating member 92a yet to be described. With a view to axial fixation of the bearing sleeve 35 and/or of the protective sleeve 35a, a positive connection 40 to an annular groove 40a and a ring pivot 40b set therein is provided which engages automatically upon insertion by reason of the elastically deformable material. By virtue of the protruding elastic or flexible protective sleeve 35a, impairments resulting from vibration in the course of treatment in the event of contact of the tool shank with adjacent body parts, teeth for example, are avoided. Within the scope of the invention the protective sleeve may also be arranged and fixed as a separate component only on the tool shank 25, for example it may be pushed onto it in elastically clamping manner or fixed thereon by means of a corresponding positive connection 40.

In the rear region of the oscillating rod 4a the bearing which is elastically yielding radially and axially for the oscillating rod 4a is formed by a bearing ring 42 made of elastically deformable material such as plastic or rubber, in particular an O-ring seal, in which the oscillating rod 4a is seated subject to external contact, the bearing ring 42 being received and supported in a sleeve 43 surrounding the oscillating rod 4a with a radial annular space 43a or in a bearing part 44 extending rearwards from said sleeve, said sleeve or said bearing part being supported in the sleeve casing 41 in radially and axially immovable manner or preferably supported so as to be movable contrary to a restoring force, in particular being pushed in from the rear and bearing with a frontal shoulder face against a rear shoulder face of the sleeve casing 41. The bearing part 44 comprises a frontal sleeve attachment 45 which surrounds the oscillating rod 4a subject to a radial spacing, the rear end of the oscillating rod 4a terminating in a free space 46 of the bearing part 44. The front sleeve attachment 45 is connected to the sleeve 43 in mutually overlapping arrangement, is preferably slipped over or inserted in closing manner and sealed by a seal which is formed here by the bearing ring 42.

The oscillating rod 4a with the associated bearing elements may be arranged coaxially in relation to the longitudinal centre axis 26. With the present configuration the longitudinal centre axis 26a of the oscillating rod 4a is offset with respect to the longitudinal centre axis of the front end region of the gripping sleeve 3 and of the bearing sleeve 35 towards the side facing away from the laterally arranged tool body 8a and is consequently arranged eccentrically, the outlet opening 11 and the associated through-channel 11a in which the optical waveguide 9a is received being arranged with respect to the oscillating rod 4a towards the side facing the tool, here in the correspondingly eccentric bearing sleeve 35. The rear end of the optical waveguide 9*a* is arranged by means of a bearing sleeve 47 in an extension of the coupling recess 16*a*, whereby by virtue of an eccentric through-channel 44*a* in the bearing part 44 the optical waveguide 9*a* extends forwards as a part that is arcuately shaped laterally. Opposite the optical waveguide 9*a* the bearing part 44 comprises an eccentric rear pipe socket 48 which is adjoined at the rear by a sleeve projection 49*a* pertaining to a coupling sleeve 49 which is supported in the sleeve casing 41 on its own or with the bearing part 44 in the form of a combined component so as to be movable radially in all directions and movable axially contrary to a restoring force. This purpose is served by at least one bearing ring 51 surrounding the coupling sleeve 49 and made of elastically deformable material, which centres the coupling sleeve 49 by reason of its elastic restoring force and supports it radially in elastically yielding manner. The bearing ring 51 preferably comprises an inner flange 53 which engages a rear shoulder face 52 from the rear and which also supports the coupling sleeve 49 in elastically yielding manner with respect to axial movements directed rearwards. With the present configuration the structural unit formed by the coupling sleeve 49 and the bearing part 44 is supported between the inner flange 53 and the bearing ring 42 so as to be elastically yielding in both axial directions. In addition, an axially and preferably also diametrally effective bearing ring 50 made of elastically yielding material may be arranged between associated shoulder faces 41*a*, 44*b*, here between an inner shoulder of the sleeve casing 41 and an outer shoulder of the bearing part 44, whereby centring is guaranteed by reason of the elastic restoring force of the elastically yielding bearing elements, and to be specific both axially and diametrally. The bearing ring 51 is fixed positively in the axial direction, for example by its inner flange 53 bearing against a forward-directed shoulder face of a threaded sleeve 54 which is screwed into the rear end of the sleeve casing 41.

In the rear region of the plug-in/rotating coupling 16 a latching device 55 which is capable of being pressed over manually is provided for the purpose of press-over latching in the final coupling position. With the present configuration the latching device 55 comprises one or more latching elements arranged in distributed manner over the periphery in radial holes in the coupling sleeve 49 and preferably formed by spheres, formed, which latching elements can sink so far into the holes that the adially inner ends of the latching elements can engage in an annular groove in the coupling spigot 16*b*. When the plug- in/rotating coupling is pressed over manually, the latching elements are automatically pressed out of the annular groove contrary to a spring acting radially inwards in the form of a spring washer 59. The holes are tapered at their inner ends, so that the latching element(s), preferably spheres, cannot fall out inwardly when the coupling spigot 16*b* is removed.

The media lines extend in the connecting piece 17 in the form of, for example, axially parallel channels 13*a*, 15*a* which continue in the associated transverse through-plane in the form of angular channels in the coupling spigot 16*b* and in the coupling sleeve 49, the one transverse through-plane E1 being axially offset with respect to the other transverse through-plane E2 of the compressed-air line and the angular channels being designated in the coupling sleeve 49 by 13*b*, 15*b*. Adjacent to the angular channel 13*b* of the line 13 for therapeutic liquid is a tube or hose 13*c* which is connected downstream to another tube or hose 13*d* which passes through a rear wall 44*b* of the bearing part 44 in sealed manner in a feed-through sleeve 44*c* and extends in the hollow space 61 of the sleeve-shaped oscillating rod 4*a* as far as the central region thereof in which an end sleeve 62 is seated in the sleeve-shaped oscillating rod 4*a* sealed by means of one or two packing rings 62*a* and is tightly connected to the tube 13*d*, in particular is attached thereon.

Assigned to the oscillation exciter 5 is a control device for decreasing or increasing its power. By this means it is possible for its performance or, to be more exact, the intensity of the vibration or oscillations and the size of the amplitudes to be decreased or increased at will and consequently to be set. In this connection a power regulator 71 that is yet to be described in detail for automatic regulation of a preferably constant power and/or a control device 72 which is preferably capable of being set manually may be provided, with which the power or the amount of drive energy that can be supplied to the oscillation exciter 5 is variable and capable of being decreased and increased and of being set automatically or by a manual setting device 73, in steps or in infinitely variable manner. By this means the power of the treatment instrument can be adapted to the work to be performed, for example coarse and fine work or coarse, medium and fine work, or to different types of treatment and/or to tools 7 that differ with respect to shape and/or size and/or coarse and fine effectiveness or coarse, medium and/or fine effectiveness.

The manually operable setting device 73 comprises a setting member 74 which is manually accessible from outside and adjustable axially or in the peripheral direction and is in driving connection with the control device 72 or forms a control device. With the present configuration the setting member 74 is a setting sleeve 74*a* which surrounds the handpiece 2 preferably in the rear region thereof and in particular is arranged countersunk in an annular recess 75 forming a ring guide and is adjustable axially or in the peripheral direction. With the present configuration the annular recess 75 is limited at the rear by a shoulder face of the screw-in sleeve 54. From the internal shell surface of the setting sleeve 74*a* a supporting crosspiece 76 protrudes radially inwards which extends over a part of the periphery and is inserted through slots 77*a*, 77*b* in the sleeve casing 41 and in the components arranged radially inwards therefrom, here in the coupling sleeve 49 and in the bearing ring 51, subject to clearance, and bears at its inner end a segment 78 extending over a section of the periphery, which on one side prises an oblique or curved surface 79 which interacts with an adjusting member 81 operationally linked to the control device 72, as shown schematically by FIG. 3 and by FIGS. 1 and 2 in the form of an embodiment. The oblique or curved surface 79 may be arranged on the front and on the rear of the segment 78. With the present configuration, in which the setting member 74 is located in the rear end region of the handpiece 2, the oblique or curved surface 79 is arranged at the front, and the adjusting member 81 is an adjusting pin 81*a* which is displaceably supported in axially parallel manner in a guide 82 and is pressurised by the force of a spring, here a compression spring, against the oblique or curved surface 79 and consequently is capable of spanning the latter in the event of rotation of the adjusting member 74 back and forth. The guide 82 may be formed by an axially parallel bore in the coupling sleeve 49 which is supported so as to be secure against rotation.

The setting device 73 may be capable of being set in steps or in infinitely variable manner. In both cases it is advantageous to assign to the setting device 73 an immobilizing device 83 which enables the setting device 73 to be immobilised in the position that is set in the given case and thereby prevents unintentional adjustment. In this connection it may be a question of a braking device which by reason of its stiffness prevents unintentional adjustment of the adjusting member 74. With the present configuration a press-over latching device 84 with a latching element 85 guided in radially movable manner and preferably formed by a sphere is provided which upon rotation of the setting sleeve 74*a* is capable of engaging and disengaging, in a manner capable of being pressed over manually, in spherical indentations 86 arranged in series on an external shell surface of the coupling sleeve 49 in the peripheral direction, here at the bottom of the groove or of the slot 77*b*. The latching element 85 may be supported in a radial bore on the supporting crosspiece 76 so as to be radially displaceable and may be biased against the spherical indentations 86 by a compression spring 88 arranged in the bore. The adjusting member 81 acts on the oscillation exciter 5 which is capable of being set as regards its performance, so that the power thereof can be increased or decreased at will with the setting member 74.

In the present embodiment, in which the oscillation exciter5 is capable of being driven or excited pneumatically, the control device 72 may comprise a control valve 65 for the purpose of controlling the pressure p1 that is effective at the oscillation exciter 5. In this connection the setting member 74 may be connected indirectly or directly to a valve slide 66 which controls the size of a valve opening 67 as a function of the setting of the setting member 74. The valve opening 67 is located in the supply line 15, here downstream of the coupling spigot 16*b* in the region of the angular channel 15*b*. With a view to decreasing the oscillating power, the valve slide 66 is displaced with the setting device 73 in the sense of a diminution of the valve opening 67, in the present embodiment forwards, so that the valve opening 67 decreases the in-situ pressure p1 at oscillation exciter 5 in the sense of an adjustable throttle. With a view to increasing the power, the valve opening 67 is enlarged in the contrary sense, as a result of which a greater in-situ pressure p1 is set. The return of the setting member 74 may be effected by means of a retraction spring which biases the setting member 74 against the oblique or curved surface 79.

It is advantageous to provide, in addition to or instead of the control device 72 for setting the in-situ pressure p1, an automatic pressure-regulating device 71*a* having a pressure-regulating valve 71*b*, whereby said device or said valve sets a substantially constant effective pressure p1 independently of the operating pressure p2 that is present in the supply-line section 15*a*. By this means, even in the case of considerable tolerances of the effective pressure p1, substantially similar working conditions and an approximately comparable power or intensity of the tool 7 are obtained when the treatment instrument is connected to supply lines 18 and supply devices having different operating pressures p2, in particular lines and devices produced by different manufacturers.

In the case where both a control valve 65 and a regulating valve 71*b* are present, the valve slide 66 is arranged in the supply line 15, here in the axially parallel supply line section 15*b*, preferably supported so as to be longitudinally displaceable therein, whereby the valve opening 67 can be controlled by a front face of the valve slide 66. The valve slide 66 may also have a pot-like shape, whereby the valve opening 67 may be arranged in the peripheral wall of the pot shape.

Figures 2, 3:
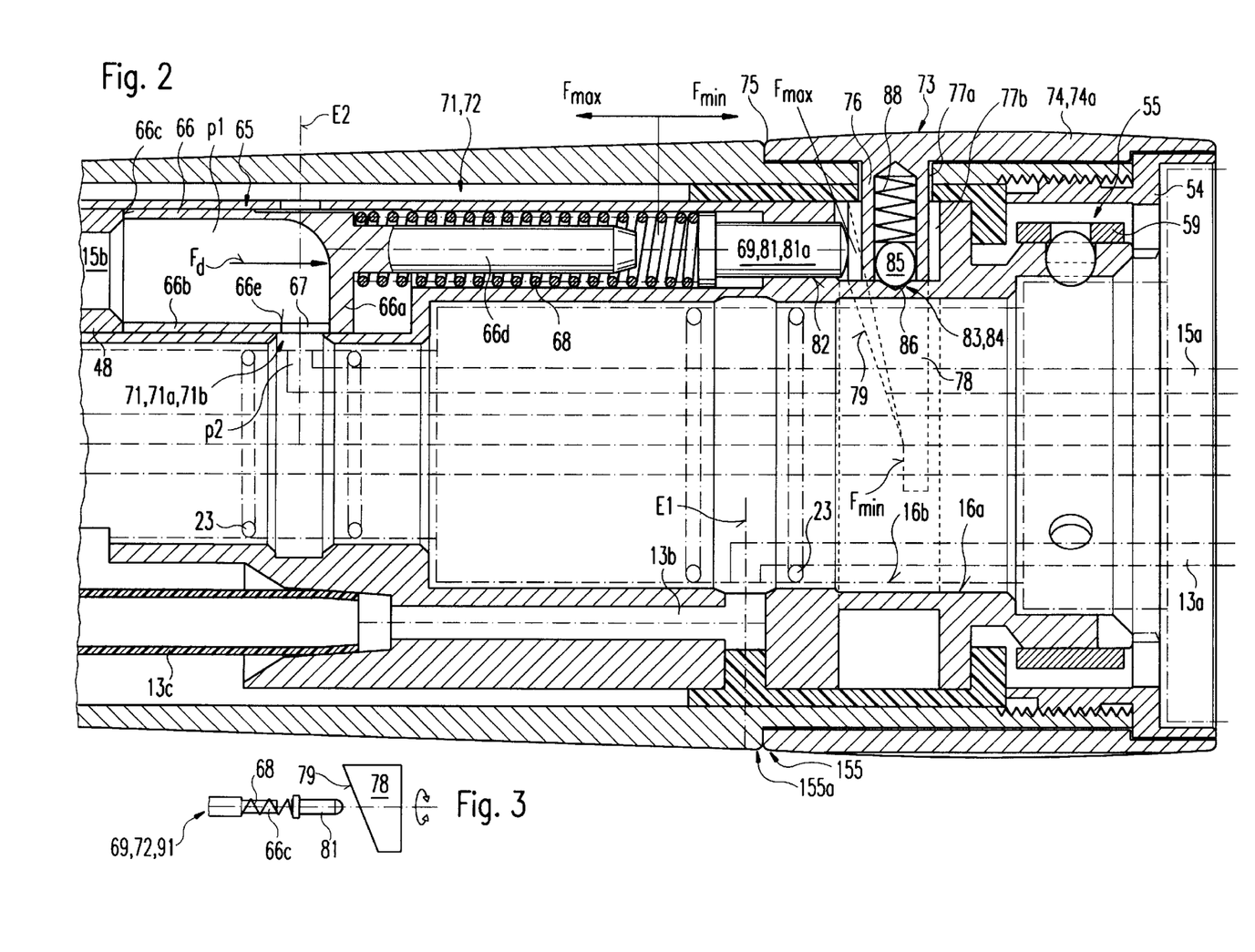
FIG. 2 the detail denoted by X in FIG. 1, in an enlarged representation.
FIG. 3 the detail according to FIG. 2 in simplified schematic representation.

In the present embodiment according to FIGS. 1 to 3 a control device 72 or a manual setting device 73 in combination with a pressure-regulating valve 71*b* are provided. The valve slide 66 is pressurised on its onefront side by the effective pressure p1 and on its other front side is biased in the contrary direction into its open position by means of a compression spring 68. With the present configuration the valve slide 66 is a circular or non-circular pot-shaped sleeve with a bottom wall 66*a* at its end facing away from the oscillation exciter 5. The valve opening 67 is arranged in the radially interior peripheral wall 66*b* so as to interact with the radial section of the supply-line section 15*b*. In the open position the valve slide 66 is tightened by the spring 68 against a stop 66*c*, here the pipe socket 48. From the valve slide 66 an expanding mandrel 66*d* extends rearwards on which the compression spring 68 is seated and supported against a rear abutment 69, here against the adjusting member 81.

In functional operation the compressed air flows from the supply-line section 15*b* through the annular gap which is present at the rear end into the hollow space 61 of the sleeve-shaped oscillating rod 4*a* which in the central region and in front of the end sleeve 62 comprises one or more radial and/or secantial flow-through holes 63, in the region of which the oscillating rod 4*a* is surrounded, subject to radial clearance, by a wobbling or vibrating sleeve 64 which is arranged, subject to axial clearance, between two stops 64*a* which may each be formed by a ring made of elastic material, for example an O-ring seal, which is seated in an annular groove in the oscillating rod 4*a*. During the perfusion of the gap between the oscillating rod 4*a* and the vibrating sleeve 64 the latter is caused to oscillate and transmits the oscillation to the oscillating rod by mechanical impact. The gap is so large that the vibrating sleeve 64 does not strike against the inner wall of the sleeve 43 surrounding it. The air or, to be more exact, exhaust air flows out of the annular space 43*a* through an air-permeable supporting ring 43*b* arranged between the oscillating rod 4*a* and the front end region of the sleeve 43, which may be perforated and may consist of elastic or yielding material such as plastic or air-permeable material such as felt, for example, into the free hollow space 41*b* of the sleeve casing 41 and through a suitable opening (not represented), in particular a rear opening, in the sleeve casing 41 into the open air or, for example, through the channel 44*a* and through a suitable outlet channel in the coupling spigot 16*b* back into the open air. The supporting ring 43*b* is axially fixed, here between an optionally conical shoulder face on the oscillating rod 4*a* and an inner flange of the sleeve 43.

The sleeve 43 in conjunction with the supporting ring 43*b* forms an inner casing or an encapsulation of the oscillation exciter 5, as a result of which a significant decrease in noise is achieved in simple and inexpensive manner.

The valve opening 67 is an adjustable throttle which produces a drop in pressure that determines the effective pressure p1. If the operating pressure p2 is greater or less than a certain value, firstly the pressure p1 also changes which is generated by the compression force Fd acting on the valve slide 66 contrary to the spring 68, whereby the position of the edge 66*e* of the opening determining the size of the valve opening 67 and consequently also the size of the throttle which generates the effective pressure p1 is determined by the equilibrium of the spring force and the compression force Fd. In functional operation the valve slide 66 assumes an operational position remote from the stop position which is represented (non-operational position), in which, for example at a medium operating pressure p2, the valve opening 67 assumes a size in the medium range. At a lower operating pressure p2 the valve slide 66 is displaced into an equilibrium position (here to the left) in which it controls a larger valve opening 67. At an increased operating pressure p2 the valve slide 66 assumes an equilibrium position (here displaced to the right) in which it controls a smaller valve opening 67. By reason of this function the regulating valve 71b automatically regulates a substantially constant in-situ pressure p1 at different operating pressures within a definable pressure range. This pressure regulation functions both when a setting device 73 or some other control device 72 is absent and when—as in the present embodiment—the pressure regulator or power regulator 71 is arranged in combination with the setting device 73 or some other control device 72 or even when—as in the present embodiment—the manual setting device 73 or some other control device 72 acts on the pressure-regulating valve 71b or on the valve slide 66 thereof. A common valve opening 67 for the pressure-regulating valve 71b and the manual setting device 73 or some other control device 72 is preferably present. By this means the cost of construction and manufacture is reduced considerably and the structural design is simplified.

In the present embodiment the biasing force of the valve spring 68 is changed by means of the setting device 73 and, to be specific, is increased for a high power requirement and decreased for a lower power requirement. For a higher power requirement the adjusting member 81 is consequently displaced in the direction of the control valve or regulating valve 65, 71b and for a lower power requirement it is distanced from the control valve or regulating valve 65, 71b—ie, is displaced towards the rear, as made clear by the reference symbols Fmin and Fmax. In the present embodiment the power of the power regulator 71 is changed by means of the setting device 73 in the sense of an increase or decrease in the power that is capable of being output at the tool 7 and, to be specific, independently of the magnitude of the operating pressure p2. In the case of a configuration without reulating valve 71b, which is possible within the scope of the invention, the power can likewise be decreased and increased at will by means of the manual setting device 73 or some other control device 75, and, to be specific, in a manner dependent on the operating pressure p2 that is present, whereby the adjusting member 81 likewise acts on the valve slide 66 of the control valve 65 which now performs a control function. To this end the adjusting member 81 may be directly connected to the valve slide 66, for example it may be formed by an expanding mandrel 66d of required length.

By this means it is possible for the treatment instrument 1 to be adapted not only to different treatment methods but also to tools 7 of differing shape and/or size and/or abrasive erosion capacity, for example coarse and fine or coarse, medium and fine, in which connection a coordination taking account of tools 7 of differing masses and/or shapes is also possible. In addition, with the setting device 73 according to the invention it is possible for states of oscillation interfering with one another to be largely eliminated by changing the amplitudes of oscillation.

The principal direction of the amplitude of oscillation is directed substantially transverse to the oscillating part 4a and consequently in the longitudinal direction of the tool 7. However, by reason of the radial and axial elastically yielding support of the oscillating part 4a, spatial oscillations arise that are caused, inter alia, by resonances, so that the tool 7 is also abrasively effective in the transverse direction.

In the present embodiment the oscillating or vibrating drive has a frequency in the sonic or ultrasonic range from about 4 to 8 kHz, preferably about 6 kHz, in which connection an amplitude of the spatial movements from about 0.05 mm to 0.2 mm, in particular about 0.1 mm, results in the region of the tool 7.

The treatment instrument according to the invention is therefore particularly well suited for different tools 7 that are assigned to the treatment instrument in the form of a tool assortment and that differ from one another by reason of differing shape and/or size and/or purpose.

The retaining device 6 according to the invention enables not only secure retention of the tool 7 on the handpiece shank 25 but also easy, easy-to-handle and rapid clamping or detaching of the tool 7. With a view to detaching and moving the locking part 29 out of the locking recess 28 an actuating member 91 is movably supported in a guide as a captive component in the front end region of the handpiece shank 25 between a position of readiness and a detaching position. The actuating member 91 is directly or indirectly connected to the locking part 29, its direction of motion between the position of readiness and the detaching position being parallel to the direction of motion of the locking part 29—ie, directed radially with respect to the tool shank 8. In the present embodiment the actuating member is an actuating slide 92 which is manually accessible laterally and/or from the side of the handpiece shank 25 facing away from the tool 7 and is preferably formed by an actuating sleeve made of plastic or, preferably, metal surrounding the tool shank 25 and capable of being displaced thereon in the longitudinal direction thereof, whereby the hollow cylindrical shell surface of the handpiece shank 25 forms a longitudinal guide 93 for the actuating slide 92. According to FIG. 4 the actuating sleeve 92a is so long that it protrudes beyond the plug-in hole 27 on both sides, whereby it comprises, in alignment with the plug-in hole 27, a plug-in recess 94 on its side facing the tool 7, which, taking the adjustment path of the actuating sleeve 92a into account, is formed by an elongated hole which may narrow in the form of a slot towards the rear of the actuating sleeve 92a. Offset forward with respect to the plug-in recess 94, the actuating sleeve 92a comprises two with respect to the longitudinal centre axis 27a of the plug-in hole 27 a through-hole 95 which takes the form of a through-hole in the handpiece shank 25, in which a transverse pin 96 is supported preferably with caps 97 inserted on it at the end, whereby the transverse pin 96 or the caps 97 is/are inserted through a slot 98 preferably narrowing towards the front in the front end region of the handpiece shank 25, subject to clearance. By this means a rotation-preventing device for the actuating sleeve 92a is created. On the central region of the transverse pin 96 the locking part 29 is seated with the aid of a corresponding transverse hole 99 which in the case of the present embodiment is formed in graduated manner for the caps 97. The locking part 29 is located in a coaxial location hole 101 in the handpiece shank 25 narrowing towards the front, in the front region of which an internal thread is arranged. The locking part 29 comprises at its rear a locking lug 29a in the form of a rounded dome, the flanks of which may be so steep that over-pressing of the latching device 102 so formed by means of axial traction on the tool 7 is not possible, or may be so flat that automatic displacement of the locking lug 29a out of the locking recess 28 is possible bpulling on the tool 7. At the front the locking part 29 is formed with a torus as a spring plate 103, a compression spring 104 between the spring plate 103 and a spring plate 105 being arranged on a screw top 106 which is screwed into the location hole 101. The screw top 106 may be covered on the front by a preferably convexly rounded cap 107 preferably made of plastic which is latched to the screw top 106 by means of a latching pin 109 set into a latching hole 108. For the purpose of screwing and unscrewing, said screw top comprises a tool-application element, here two axially parallel blind holes 111, into which a tool having corresponding driving spigots is capable of being introduced. With a view to sealing the longitudinal guide 93, packing rings 112 are provided on both sides of the plug-in hole 27, preferably in the form of O-ring seals arranged in annular grooves located in the external shell surface of the handpiece shank 25 or in the internal shell surface of the actuating sleeve 92a. The rear bottom face of the slots 98 forms a stop 98a for the rearward-directed movement of the locking part 29 in which the locking lug 29a projects into the plug-in hole 27. The latching device 102 already described thus far for the tool shank 8 is advantageous operationally and for reasons of advantageous and simple handling as well as secure retention. Upon insertion of the tool shank 8 into the plug-in hole 27 the latching or locking lug 29a is driven out into its release position by means of an insertion bevel 113 or insertion curvature which is preferably also present at the free end of the tool shank 8, so that the tool shank 8 can be pushed in further until its free end impinges against the inner wall of the actuating sleeve 92a. In this position the locking lug 29a automatically springs into the associated locking recess 28, whereby the surfaces of the locking recess 28 preferably form the movement-stopping device in the locking position.

If the locking recess 28 is formed by an annular groove, a retaining device is created for the tool shank 8, with which a rotation of the tool in the retaining device 6 is possible, whereby an unbraked—ie, free—rotary capacity is also guaranteed when the stop 98a is so arranged that although the locking lug 29a is set into the annular groove it does not press against the bottom of the annular groove or presses against it only lightly.

In the present configuration with several spherical indentations 31 arranged in distributed manner on the periphery a rotary-position setting device 114 which enables different rotary positions of the tool 7 is created by virtue of the fact that the latching in the respectively associated spherical indentation 31 forms a rotation-preventing device.

It is possible to form this rotary-position setting device 114 in such a way that when a certain torque is exceeded the latching device 110 is pressed over automatically and the locking lug 29a is automatically pressed out of the associated spherical indentation 31. As a result, all that is required is an adaptation of the flank 29b of the locking lug 29a and/or of the conical surfaces of the spherical indentations 31 to a particular angle at which, taking the particular torque into account, detachment of the latching device 110 is to be effected automatically.

With a view to arbitrary detachment of the latching device 102, for example if a tool 7 is to be detached or exchanged, the actuating member 91 is displaced forwards manually by finger pressure in the direction of the arrow 115 contrary to the force of the spring 104, whereby the latching device 102 is detached and the tool shank 8 can be drawn out of the retaining device 6.

In the case of a latching device described previously an axial continuation of the line 13 in the form of a channel 13e in the handpiece shank 25 as far as the plug-in hole 27 and radial and axial channel sections 13f and 13g adjacent thereto that are present in the tool shank 8 enables the supply of the therapeutic liquid to the treatment site, whereby the liquid may flow out at outlet openings, which are not represented, in the region of the abrasive working surfaces of the tool 7. Alternatively, or in addition, a longitudinal groove 13h extending from the transverse region of the locking recess 28 to the tool body 8a may also be provided in the shell surface of the tool shank 8, through which therapeutic agent can flow on the outside of the tool body 8a to the treatment site.

It is moreover advantageous to form the retaining device 6 with a device 116 for ejecting the tool shank 8 from the retaining device 6. Such a device 116 may be formed with a wedge mechanism and a wedge surface 117 or curved surface which upon movement of the actuating member 91 into its detaching position presses against the tool shank and displaces it in its extraction direction. With the present configuration the wedge surface 117 is formed by the rear flank of a preferably conical spherical indentation 118 in the internal shell surface of the actuating sleeve 92a, the conical surface 117 being so arranged that in the position of readiness of the actuating sleeve 92a according to FIG. 4 the tool shank 8 bears against a low point of the conical surface 117 or is spaced therefrom by a short distance. The front end of the tool shank 8 is preferably spherically or conically rounded, in order that the conical surface 117 is applied in the central region of the front face. With the present configuration a domed pressure element or preferably a sphere 119 is arranged at the free end of the tool shank 8 partly countersunk into an end recess 121 and is secured therein to prevent it from falling out. By this means a substantially central point of attack is created for the wedge surface 117 on the tool shank 8. If the sphere 119 is retained in the recess 121 so as to be freely rotatable, the friction forces are significantly reduced upon ejection of the tool shank 8 and handling is thereby facilitated.

Since an actuating member 91 is assigned to the locking part 29 with a view to disengagement, for the purpose of achieving greater axial locking forces the flanks 29b may be formed so steeply, or even at a right angle to the shank axis 27a, that it is not possible for the locking part 29 to be pressed over or driven out of the locking recess 28.

In addition to the latching device 102 a latching device 125 may be provided, preferably located opposite it, in the present configuration to the rear of the plug-in hole 27, having a locking lug 125a which is likewise rounded in the shape of a dome on a locking part 125b which is capable of being displaced between a locking position set into the locking recess 28 and a release position releasing said locking position and is biased by the force of a spring, here a compression spring 126, into its locking position, so that the locking lug 125a engages automatically upon insertion of the tool shank 8. With this configuration, however, no direct mechanical connection is provided between the actuating member 91 and the locking part 125b. Therefore with this latching device 124 the flanks 29b of the locking lug 125a or of the locking recess 28 or spherical indentations 31 should be formed to be so flat that in the event of a displacement of the tool shank 8 in the plug-in hole 27 the locking lug 125a is automatically driven out of the locking recess 28 and this latching device 125 is consequently capable of being pressed over manually.

Within the scope of the invention it is possible to form the retaining device 6 with the latching device 125 only—ie, without the latching device 102 and also without the actuating member 91. With such a configuration the locking lug 125a engages automatically upon insertion of the tool shank 8 and it is possible for the latching device 125 to be automatically detached by exerting an axial traction force on the tool 7, whereby the locking lug 125a is driven out of the locking recess 28. With the tool 7 removed, the locking lug 125a or the locking part 125b is positively prevented from falling into the plug-in hole 27.

With the present configuration the locking lug 125a is formed on a cylindrical pin 125c with a rear flange 125d which is displaceably supported transversely in relation to the tool shank 8 in a guide bushing 127 between its locking position and its release position. The compression spring 126 biasing the pin 125c against the tool shank 8 is arranged in the guide bushing 127 and supported at the rear on a shoulder face. The guide bushing 127 is inserted from the front into a corresponding threaded hole 128 and is screwed tightly therein. At the front end of the guide bushing 127 a rearward-directed shoulder face 129 is provided which forms a stop 131 preventing the pin 125c from falling out. Moreover, this latching device 125 may be formed so as to correspond to the latching device 102. For the passage of the media line 13 the pin 25c comprises an axial through-channel 13i.

Figure 5:
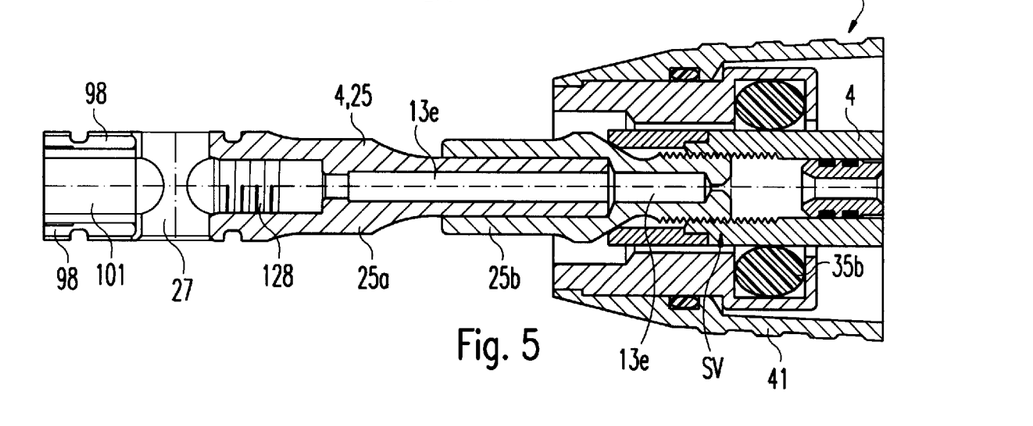
FIG. 5 the front end region of a treatment instrument in modified configuration, in axial section.
Figure 6:
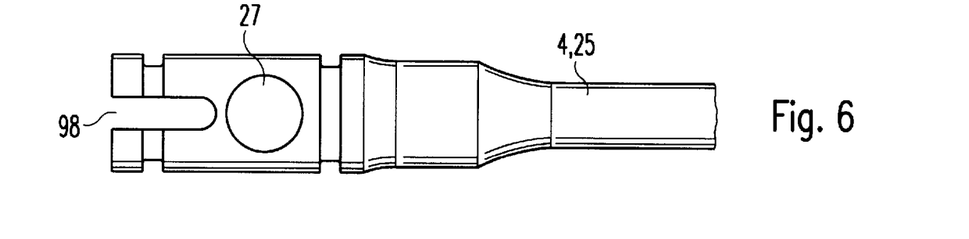
FIG. 6 a handpiece shank of the treatment instrument according to FIG. 5 in top view.

In FIG. 5 another embodiment is represented, in which the handpiece shank 25 protruding beyond the gripping sleeve or the sleeve casing 41 is formed as a separate component which by virtue of a detachable connection, preferably a screw connection SV, is coaxially connected to the preferably rod-shaped oscillating part 4a. The screw connection SV may be arranged countersunk in the front end region of the sleeve casing 41 and may be formed by a threaded spigot at the rear end of the handpiece shank 25 which is screwed into a coaxial threaded hole in the oscillating part 4. The screw connection SV may be provided in the case where a bearing sleeve 35 made of elastically deformable material according to FIG. 1 is present or in the case where a bearing ring 35b made of elastically deformable material is present which elastically centres the oscillating part 4 in comparable manner and is seated in an annular groove of an inner sleeve which is inserted in the front end region of the gripping sleeve or of the sleeve casing 41. Outside the sleeve casing 41 or the bearing sleeve 35 the handpiece shank 25 comprises a tool-application element for the purpose of screw-fastening or unscrewing, for example a hexagon. With the present configuration the handpiece shank 25 consists of two shank parts 25a, 25b arranged coaxially in series which, for example, are fitted into one another in the form of a socket joint and are fastened to one another, for example by adhesion or by interference fit, in the spigot-and-socket joint.

Figure 7:
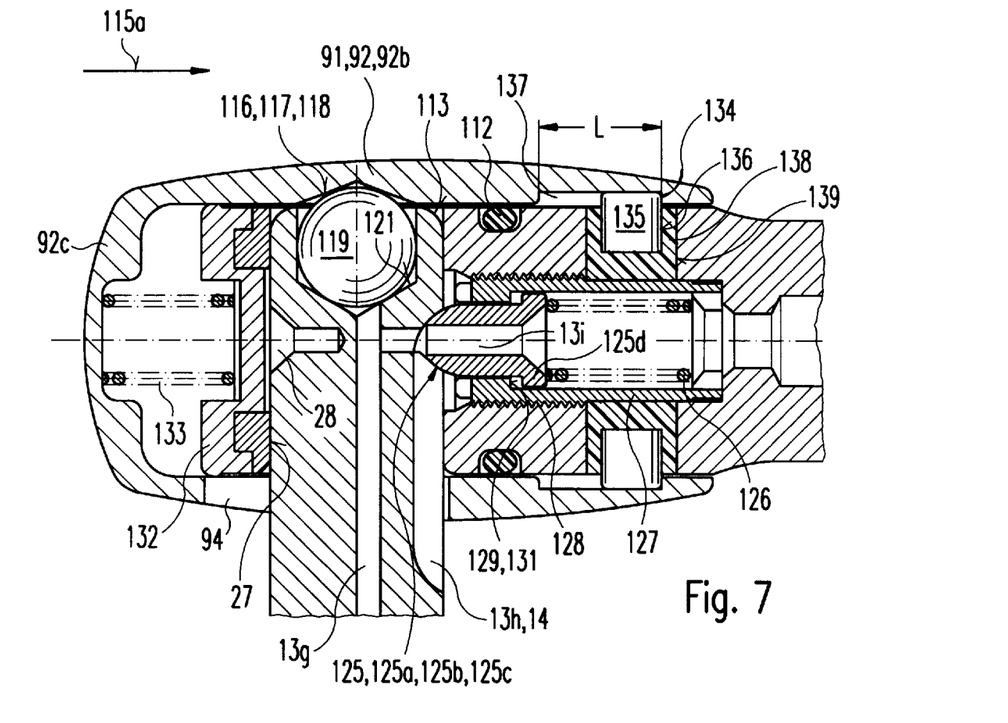
FIG. 7 the detail denoted by Y in FIG. 1, namely a retaining device for a treatment tool in the front end region of the treatment instrument, in axial section in modified configuration.

In order to facilitate detachment of the tool shank 8, the retaining device 6 according to FIG. 7 may also be formed with a device 116 for ejecting the tool shank 8. This purpose may be served by an actuating member 91 likewise in the form of an actuating sleeve which is supported so as to be axially displaceable on the front end region of the handpiece shank 25. This actuating sleeve 92b may be closed at the front by a front wall 92c, whereby a compression spring 133 arranged between the front wall 92c and a spring plate 132 biases the actuating sleeve 92b into its position of readiness in which, in contrast to the configuration according to FIG. 4, it is located in a frontal end position in which the frontal flank of the spherical indentation 118 forms the wedge surface 117. In the event of a displacement of the actuating sleeve 92b rearwards in accordance with arrow 115a by axial pressure on its front wall 92c the locking lug 125a is pressed out of the locking recess 28 and the tool shank 8 is pressed out of the plug-in hole 27 by the wedge surface 117. In order to enable this movement, the plug-in recess 94 is lengthened by the extent of the forward movement. In the position of readiness according to FIG. 7 the axial movement is limited by a stop 134 which may be formed by one or two stop pins 135 arranged opposite one another which are supported in radial holes 136 in the handpiece shank 25 in radially displaceable manner, are biased radially outwards by the force of a spring and are each set into a longitudinal groove 137 in the internal shell surface of the actuating sleeve 92b, the length L of which is greater by the extent of the axial movement than the associated cross-sectional dimension of the stop pin 134, so that the actuating sleeve 92b can be displaced in its longitudinal position. The lateral surfaces of the longitudinal grooves 137 form with the pins 135 set therein a rotation-preventing device for the actuating sleeve 92b. With the present configuration each of the stop pins 135 is received in a pot-shaped bushing 138 made of elastically deformable material such as rubber or plastic which are seated in correspondingly larger holes 139.

Figure 8:
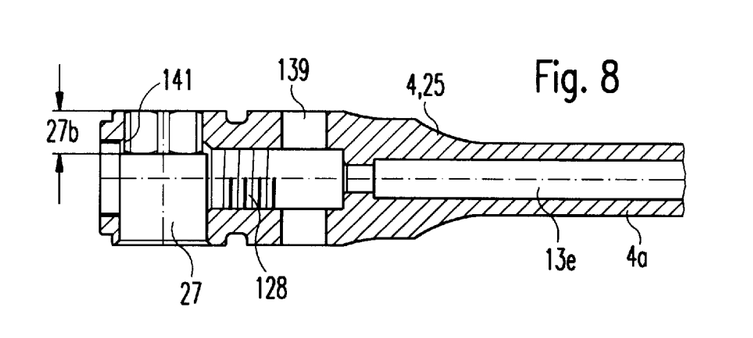
FIG. 8 the front end of a handpiece shank of the retaining device according to FIG. 7, in partially modified configuration in axial section.
Figure 9:
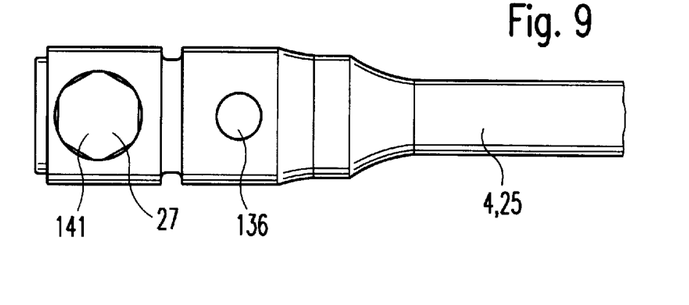
FIG. 9 the handpiece shank according to FIG. 8 in top view.

The rotary-position setting device 114 may be formed, instead of by spherical indentations 31 in the shank 8, by a plug socket 141, whereby the latter and the tool shank 8 which is capable of being inserted therein each have such a non-circular and matching cross-sectional shape that the tool shank 8 is capable of being inserted therein in two or more positions that are rotated in relation to one another. In the case where a non-circular plug socket 141 is present, instead of spherical indentations 31 an annular groove of corresponding cross-sectional shape may be provided. The cross-sectional shape of the plug socket 141 and of the tool shank 8 preferably has three or more, in particular six, regular corners. The cross-sectional shape may also be formed in the sense of a multi-tooth connection. The plug socket 141 does not need to extend over the entire length of the plug-in hole 27. For good functioning it is sufficient if only a section or the free end region of the tool shank 8 and a matching inner section or end region 27b of the plug-in hole 27 are formed as a plug socket 141, as FIGS. 8 and 9 show. With this configuration the locking recess 28 may be formed in simple manner as an annular groove.

Figure 10:
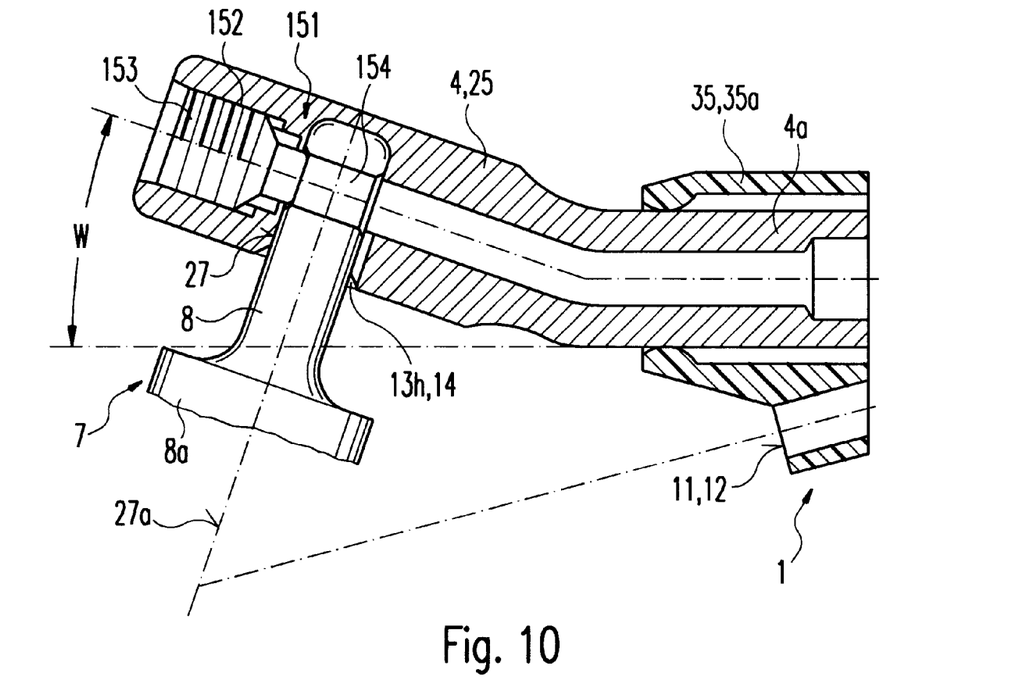
FIG. 10 the detail denoted by Y in FIG. 1, namely a retaining device for a tool arranged in the front end region of the treatment instrument, in axial section in further modified configuration.

With the configuration according to FIG. 10, in which like or comparable parts are provided with like reference symbols, instead of a latching device a screw connection or clamping connection 151 with a locking screw 153 which is preferably screwed from the front into a threaded hole 152 in the handpiece shank 25 is provided which is capable of being screwed into an annular groove 154 or into one of several locking recesses in the tool shank 8 arranged in distributed manner on the periphery in such a way that it presses against the tool shank 8 which is received in the plug-in hole 27 or is set into the respective recess subject to rotary clearance, as previously described, in order to form a rotatable retaining device or a rotary-position setting device. Also with this configuration therapeutic liquid can be conducted by means of a radial and/or axial channel in the tool shank 8 to at least one of the abrasive working surfaces of the tool 7 or by means of a longitudinal groove 13h arranged on the tool shank 8 or in the wall of the plug-in hole 27 which enables discharge of the therapeutic medium on the outside of the tool 7.

Figure 11:
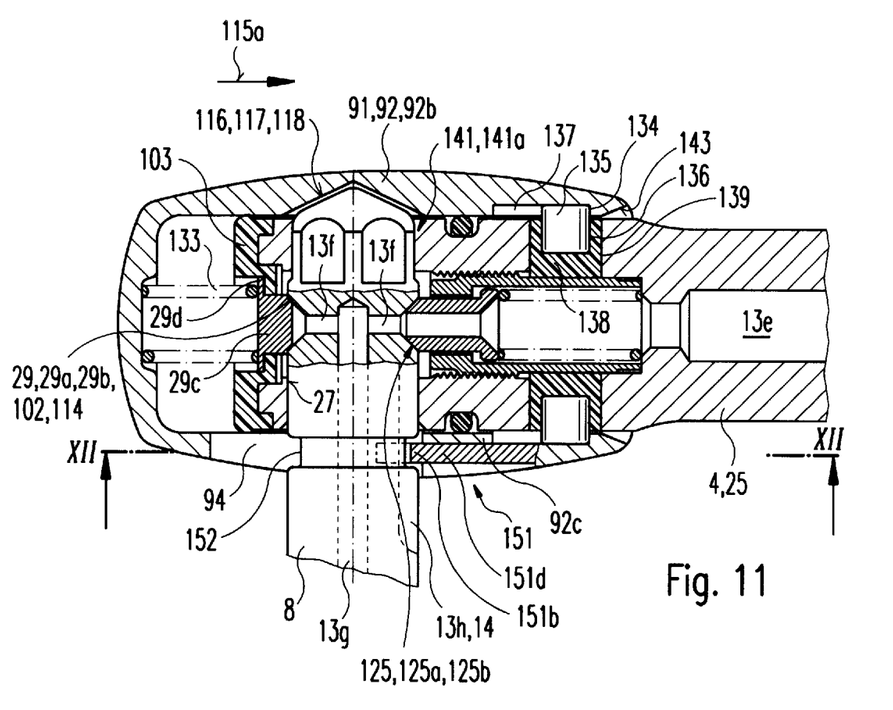
FIG. 11 a view corresponding to FIG. 10, in further modified configuration.
Figure 12:
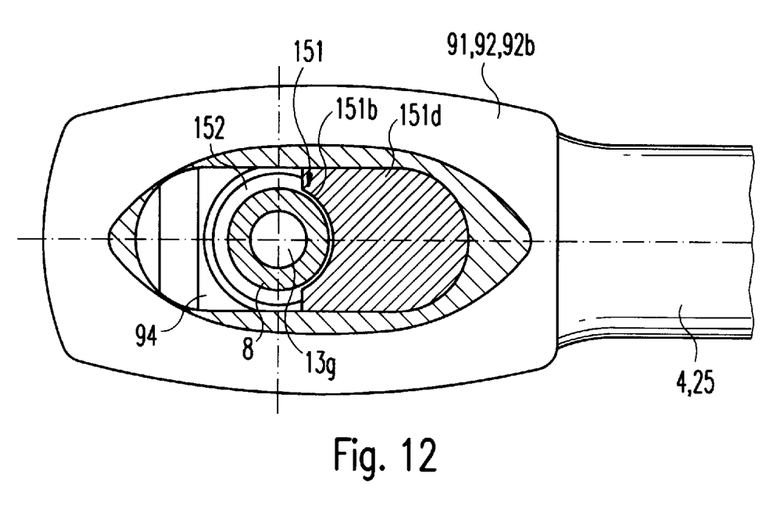
FIG. 12 section XII—XII in FIG. 11.

FIGS. 11 and 12 show several embodiments which may be arranged in combination or, in each instance, individually, whereby like or comparable parts are provided with like reference symbols.

An actuating sleeve 92a corresponding to the embodiment according to FIG. 7 is provided which is to be displaced rearwards in the direction of the arrow 115a in order to detach the tool shank 8, as previously described. A plug socket 141 as described previously is also provided between the tool shank 8 and the handpiece shank 25.

With a view to axial retention of the tool shank 8, instead of or in addition to the latching device 125 a locking lug 29b may be provided which by virtue of the force of a spring is set or biased into a spherical indentation 31 or annular groove in the tool shank 8 but which is capable of being removed from or driven out of the spherical indentation 31 or the annular groove independently of a movement of the actuating member 91. Starting from the configuration according to FIG. 7, to this end the locking lug 29b is pressurised into its locking position by the spring 133, whereby the locking lug 29b may be moulded in one piece on the spring plate 103 or may be mounted onto the latter as a separate component and may preferably be pressurised directly by the compression spring 133. With the present configuration the locking lug 29b is moulded onto a prismatic or cylindrical spigot 29c which is inserted from the front into a hole in the spring plate 132 and comprises on its end facing away from the lug a flange 29d which bears against the side of the spring plate 132 facing away from the plug-in hole 27, preferably against the graduated face of a graduated hole. Both with the configuration according to FIG. 4 and with the configuration according to FIG. 11 the locking lug 29b may have, instead of a convexly rounded shape, oblique surfaces or a truncated conical surface on a truncated lug which is set only slightly into the spherical indentation 31 or the annular groove.

It is advantageous furthermore to arrange on the rear edge of the actuating sleeve 92b, in alignment with the longitudinal groove or grooves 137, in each instance an insertion curvature or insertion bevel 143 diverging towards the rear, as a result of which the assembly and disassembly of the actuating sleeve 92b are significantly facilitated.

When the actuating sleeve 92b is pushed on from the front the insertion bevel 143 provides for automatic spring deflection of the associated stop pin 135 which automatically engages the associated annular groove 137 behind the stop 134. As FIG. 11 clearly shows, the insertion bevel 143 terminates above the associated bushing 138. By this means it is possible, with a view to disassembling the actuating sleeve 92b, to set a pointed tool, for example a screwdriver, into the wedge of the insertion bevel 143 and to insert the bushing 138 with the associated stop pin 135 so far that the actuating sleeve 92b can be withdrawn.

With the configuration according to FIGS. 11 and 12 a latching device 151 for locking the tool shank 8 in its position received in the retaining device 6 is also, said latching device 151 comprising a locking lug 151b on a latching or locking part 151d which is fly connected to the actuating member 92, here the actuating sleeve 92b, and is consequently capable of being moved with the actuating slide 92 and forms a motive unit. This locking lug 151b may be formed by a transverse crosspiece on the actuating slide 92 which in the position of readiness protrudes into the plug-in hole 27 or into the projection thereof or extends secantially in relation thereto and is set into a latching recess 152 in the tool shank 8, which may be an annular groove. The locking lug 151b may—viewed along the plug-in hole 27—be concavely shaped so as to conform to the cross-sectional shape of the bottom of the annular groove, for example it may be rounded, so that it is capable of encompassing the tool shank 8 in the shape of a crescent. Opposite the locking lug 151b the plug-in recess 94 for the tool shank 8 is lengthened so that the actuating slide 92 is capable of being displaced into its detaching position which is not represented, here displaced to the right, in which the locking lug 151b is moved out of the locking recess 152.

This latching device 151, which is preferably arranged on the tool side of the handpiece shank, may be provided instead of or in addition to the latching device 102 and/or 125. The device 116 for ejecting the tool shank 8 may also be provided. In this case, upon displacement of the actuating slide 92 into its detaching position the locking lug 151b is directly pushed out of the locking recess 152 and the tool shank 8 is simultaneously pushed out by the wedge surface 117.

With the present configuration the locking lug 151b is formed by a flat disc which is inserted and fastened in a recess 154 laterally adjacent to the plug-in recess 94, for example by adhesion or welding. The recess 154 may be formed so as to be less deep than the thickness of the peripheral wall of the actuating sleeve 92a, so that a wall part 92c remains against which the disc is able to abut.

The handpiece shank 25 and the parts of the retaining device 6 may consist of corrosion-resistant metal and/or plastic. In the case of the embodiments previously described the parts represented by parallel hashing consist of metal and the parts provided with cross-hatching consist of plastic.

The configurations according to the invention also result in an advantageous tool configuration in the region of a tool shank 8. In this connection it is to be emphasised that the tool shank 8 comprises locking recesses which serve to enable axial locking and to prevent rotation. For the purpose of preventing rotation, use is made of the spherical indentations 31 and/or the plug-in spigot 141a on the tool shank 8 of non-circular, for example hexagonal, cross-section which is preferably arranged on the free end of the tool shank 8. In the case of a regular arrangement of this polygon or of the spherical indentations 31 it is also possible for a rotary-position setting device for the tool 7 to be realised which enables arrangement of the tool 7 in different rotary positions. If a polygonal plug-in spigot 141a is present, instead of several spherical indentations 131 an annular groove may be provided in the tool shank 8. In the case of a tool 5 that does not need to be set in different rotary positions the latching recess 152 may be formed by a lateral recess. An annular recess is particularly well suited for different rotary positions. If a plug-in spigot 141a of non-circular cross-section is present as a rotation-preventing device, the locking recess 152 may be provided in addition to or instead of the spherical indentations 31 or an annular groove forming them. For the supply of the therapeutic medium or coolant the inner channel section 13g which opens out within or above one or more working surfaces of the tool 5 and/or the outer longitudinal groove 13h may be provided, which are connected to the supply line extending axially in the handpiece shank. One or two outlet openings 13i formed by branches are represented in FIG. 1 by way of example.

With a view to carrying out different processing operations different tools 7 may be assigned to the treatment instrument 1, with which it can optionally be equipped. In this connection it may be a question of tools 7 of, for example, differing shape and/or mass and/or physical characteristic of the abrasive working surface, for example coarse, medium, fine, and/or of tools 7 that are adapted or not adapted for a supply of a therapeutic medium, for example cooling liquid. For such different tools thee may be different power requirements in order to achieve optimal functioning or performance. In the case of tools 7 of differing mass this may be due to the fact that the mass oscillation for a power setting of specific magnitude is particularly favourable, for example taking account of oscillation resonances. In the case of tools 7 with working surfaces having differing physical characteristics such as, for example, coarse, medium or fine, a power setting of specific magnitude is likewise advantageous for the purpose of enhancing effectiveness. In addition, with this criterion it has to be taken into account that the working surfaces may have a tendency to be affected by shavings and that a specific power setting is also advantageous for this reason. A power setting of specific magnitude is also advantageous in the case of tools 7 that operate with a cooling liquid or in the dry state. It is therefore advantageous, and serves to enable simpler handling, if markings 155 for the setting member 74 are so arranged on the treatment instrument 1 that in the event of positional correspondence of the setting member 74 in the sense of the marking or of a certain marking a power is set that is advantageous for an assigned tool 7 having a corresponding marking 56. It may be a question of colour markings or other markings, for example symbols, to which an associated index 155a is assigned in each instance on the setting path of the treatment instrument with a view to positional correspondence. With the present configuration one or more markings 155 and one or more associated indices 155a may be arranged on the setting member 74 and on the gripping sleeve or on the sleeve casing 41, as is represented in simplified manner, for example in the form of a scale, with the markings 155 arranged on the one part and the at least one index 155a arranged on the other part. The corresponding marking 156 may be arranged in each instance on the tools 7, for example on the tool shank 8 in the vicinity of the tool head. Different colours are particularly well suited for differentiating one pair of markings 155, 155a, 156 from another pair of markings 155, 155a, 156, whereby markings 155, 155a, 156 corresponding to one another preferably have the same colour.

Figure 13:
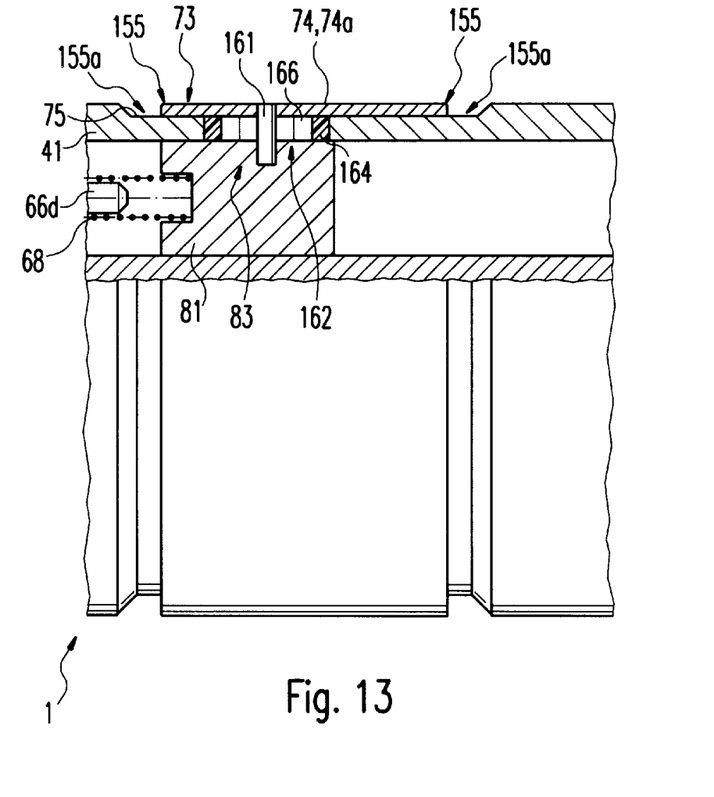
FIG. 13 a longitudinal section of a treatment instrument according to the invention, in modified configuration in axial section.
Figure 14:
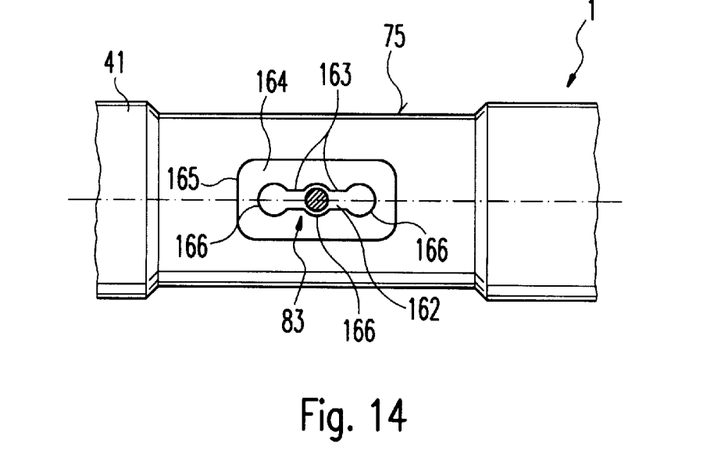
FIG. 14 the longitudinal section according to FIG. 13 in top view.

In the case of the embodiment according to FIGS. 13 and 14, in which like or comparable parts are provided with like reference symbols, the setting device 73 comprises a setting member 74, preferably likewise in the form of a setting sleeve 74a which is axially displaceable in the correspondingly longer groove 75 and capable of being immobilised in the respective setting position in infinitely variable manner or in steps by means of the immobilising device 83. With this configuration the adjusting member 81 is rigidly connected to the setting member 74 by means of a radial connecting pin 161, whereby the connecting pin 161 passes through a setting groove 162 extending lengthwise in the sleeve casing and whereby the groove walls 163 directed lengthwise clamp the connecting pin 161 so strongly between themselves that the connecting pin is capable of being axially displaced only with a manual application of force but is immobilised against unintentional displacement by the clamping action of the groove walls 163. To this end the setting groove 162 may be formed in an insert part 164 made of elastically deformable material, for example plastic, which is seated in a corresponding recess 165 in the sleeve casing 41. In case definite setting points are to be realised, lock-in recesses 166 in which the connecting pin 161 is capable of engaging may be arranged in one or in both groove walls 163. With the present configuration three lock-in points are arranged axially in series. In order to make this clear, in FIG. 14 the longitudinal section that is represented of the treatment instrument 1 is represented without the setting sleeve 74a.

With this configuration the markings 155, 155a and 156 may be arranged on the front edge or rear edge of the setting member 74 and on the shell surface of the sleeve casing 41 located alongside it.

What is claimed is:

1. A medical or dental treatment instrument for treating body tissue or a substitute substance, particularly by cutting, the instrument comprising:

an elongate handpiece having a front region;

a retaining device disposed at the front region of the handpiece and protruding from a shank portion of the handpiece at the front region, the retaining device formed with a plug-in hole, the plug-in hole being sized to receive a tool shank of a tool and the retaining device including a locking part;

the locking part adapted to engage a locking recess formed in the tool shank and to transversely engage the tool shank apart from the locking recess for locking the tool in the plug-in hole, the locking part being movably supported for transverse movement relative to the plug-in hole between a locking position in which the locking part engages the tool shank and a release position in which the locking part is disengaged from the tool shank, the locking part being biased in the locking position by a spring;

an actuating member, the actuating member being manually accessible from an external portion of the handpiece and being moveably supported on the retaining device for movement transverse to the plug-in hole, the locking part being coupled to the actuating member for movement therewith between the locking position and the release position; and an oscillation exciter with which the handpiece shank can be set vibrating.

2. The instrument of claim 1, wherein the locking part is adapted to engage at least one of an annular ring formed in the tool shank and a plurality of spherical indentations formed in the tool shank at equal intervals about a periphery of the tool shank.

3. A medical or dental treatment instrument for treating body tissue or a substitute substance, particularly by cutting, the instrument comprising:

an elongate handpiece having a front region;

a retaining device disposed at the front region of the handpiece and protruding from a handpiece shank at the front region, the retaining device formed with a plug-in hole, the plug-in hole being sized to receive a tool shank of a tool and the retaining device including a locking part;

the locking part adapted to engage a locking recess formed in the tool shank for locking the tool in the plug-in hole, the locking part being movably supported for transverse movement relative to the plug-in hole between a locking position in which the locking part engages the tool shank and a release position in which the locking part is disengaged from the tool shank, the locking part being biased in the locking position by a spring; and an actuating member, the actuating member comprising a sleeve surrounding the handpiece shank, the actuating member being manually accessible from an external portion of the handpiece and being moveably supported on the retaining device for movement transverse to the plug-in hole, the locking part being coupled to the actuating member for movement therewith between the locking position and the release position.

4. The instrument of claim 3, wherein the locking part is arranged on a pin, the being coupled to the sleeve and the pin extending through a slot formed in the shank of the handpiece.

5. A medical or dental treatment instrument for treating body tissue or a substitute substance, particularly by cutting, the instrument comprising:

an elongate handpiece having a front region;

a retaining device disposed at the front region of the handpiece and protruding from a handpiece shank at the front region, the retaining device formed with a plug-in hole, the plug-in hole being sized to receive a tool shank of a tool and the retaining device including a locking part;

the locking part adapted to engage a locking recess formed in the tool shank for locking the tool in the plug-in hole, the locking part being movably supported for transverse movement relative to the plug-in hole between a locking position in which the locking part engages the tool shank and a release position in which the locking part is disengaged from the tool shank, the locking part being biased in the locking position by a spring;

an actuating member, the actuating member being manually accessible from an external portion of the handpiece and being moveably supported on the retaining device for movement transverse to the plug-in hole, the locking part being coupled to the actuating member for movement therewith between the locking position and the release position; and one of an inclined plane and a wedge surface arranged between the actuating member and the tool shank to engage the tool shank as the locking part is moved from the locking position to the release position.

6. The instrument of claim 5, wherein the reduction gear is arranged to engage a spherical surface formed in an end of the tool shank and protruding axially from the end of the tool shank.

7. The instrument of claim 1, 3, or 5, wherein the locking part is one of rigidly connected and moveably connected by a spring to the actuating member.

8. The instrument of claim 3 or 5, comprising an oscillation exciter, the oscillation exciter having at least one of an automatic operating mode and a manual operating mode.

9. A medical or dental treatment instrument for treating body tissue or a substitute substance, particularly by cutting, the instrument comprising:

an elongate handpiece having a front region;

a retaining device disposed at the front region of the handpiece and protruding from a shank portion of the handpiece at the front region, the retaining device formed with a plug-in hole, the plug-in hole being sized to receive a tool shank of a tool and the retaining device including a locking part;

the locking part adapted to engage a locking recess formed in the tool shank and to transversely engage the tool shank apart from the locking recess for locking the tool in the plug-in hole, the locking part being movably supported for transverse movement relative to the plug-in hole between a locking position in which the locking part engages the tool shank and a release position in which the locking part is disengaged from the tool shank, the locking part being biased in the locking position by a spring and being displaceable from the locking position to the release position by application of axial force to the tool shank;

an actuating member, the actuating member being manually accessible from an external portion of the handpiece and being moveably supported on the retaining device for movement transverse to the plug-in hole, the locking part being coupled to the actuating member for manual movement therewith between the locking position and the release position; and an oscillation exciter with which the handpiece shank can be set vibrating.

10. The instrument of claim 1 or 9, wherein the oscillation exciter has at least one of an automatic operating mode and a manual operating mode.

11. The instrument of claim 3, wherein the retaining device is arranged on the shank of the handpiece.

12. The instrument of claim 11, wherein the plug-in hole extends transversely to the shank of the handpiece.

13. The instrument of claim 1, 3, 5 or 9, wherein the locking part comprises a convergent locking lug, the locking lug being movably supported with the locking part for engaging the locking recess with the locking part in the locking position and to displace from the locking recess upon application of an axial force to the tool shank.

14. A tool for use with an instrument according to claim 1, 3, 5 or 9, the tool comprising a working section and a shank connected to the working section, the shank formed to include at least one recess and an axial groove formed in the shank extending from an end of the shank toward the working section.

15. The tool according to claim 14, wherein the at least one recess comprises a spherical indentation.

16. The tool according to claim 14, the tool comprising at least two recesses equally spaced about a periphery of the shank.

17. The tool according to claim 14, the tool comprising a plug-in spigot of non-circular cross-section formed in the end.

* * * * *